(12) United States Patent
Ben-David et al.

(10) Patent No.: US 8,185,205 B2
(45) Date of Patent: May 22, 2012

(54) CATHETER SWITCH AND METHOD OF USING A CATHETER SWITCH IN ADMINISTERING A NERVE OR PLEXUS BLOCK

(75) Inventors: Bruce Ben-David, Pittsburgh, PA (US); Jacques Chelly, Pittsburgh, PA (US); Christopher DiBiase, Winter Garden, FL (US)

(73) Assignee: B. Braun Medical Inc., Bethlehem, PA (US)

( * ) Notice: Subject to any disclaimer, the term of this patent is extended or adjusted under 35 U.S.C. 154(b) by 1153 days.

(21) Appl. No.: 11/876,155

(22) Filed: Oct. 22, 2007

(65) Prior Publication Data

US 2009/0105693 A1    Apr. 23, 2009

(51) Int. Cl.
*A61N 1/08* (2006.01)

(52) U.S. Cl. .......... 607/38; 607/115; 607/117; 607/118; 607/148; 607/37

(58) Field of Classification Search .......... 607/115, 607/117, 118, 148, 37, 38
See application file for complete search history.

(56) References Cited

U.S. PATENT DOCUMENTS

| | | | |
|---|---|---|---|
| 3,682,162 A | | 8/1972 | Colyer |
| 4,019,519 A | * | 4/1977 | Geerling ................ 607/72 |
| 4,157,087 A | * | 6/1979 | Miller et al. .......... 600/554 |
| 4,248,238 A | * | 2/1981 | Joseph ................. 607/9 |
| 4,515,168 A | | 5/1985 | Chester et al. |
| 5,081,990 A | | 1/1992 | Deletis |
| 5,284,154 A | | 2/1994 | Raymond et al. |
| 5,713,925 A | * | 2/1998 | Sullivan et al. ........ 607/4 |
| 5,976,110 A | | 11/1999 | Greengrass et al. |
| 6,456,874 B1 | | 9/2002 | Hafer et al. |
| 6,973,346 B2 | | 12/2005 | Hafer et al. |
| 2004/0049231 A1 | | 3/2004 | Hafer |
| 2006/0217655 A1 | * | 9/2006 | Vitullo et al. ........ 604/21 |

FOREIGN PATENT DOCUMENTS

| | | |
|---|---|---|
| EP | 1002500 | 5/2000 |
| WO | WO98/33547 | 8/1998 |
| WO | WO99/04705 | 2/1999 |

* cited by examiner

*Primary Examiner* — Carl H Layno
*Assistant Examiner* — Natasha Patel
(74) *Attorney, Agent, or Firm* — RatnerPrestia

(57) ABSTRACT

A catheter switch comprising a first electrical connector for connection to a first medical device, a second electrical connector for connection to a second medical device, and a third electrical connector for connection to a signal source. The catheter switch further includes an electrical switch coupled to the first, second, and third electrical connectors. The electrical switch is configured to include at least two selectable positions, a first position in which the first electrical connector is electrically coupled to the third electrical connector and a second position in which the second electrical connector is electrically coupled to the third electrical connector. A catheter switch assembly system is also provided. The catheter switch assembly system is for selectively coupling a nerve stimulator to a needle assembly or to a catheter assembly to deliver electrical pulses thereto.

22 Claims, 5 Drawing Sheets

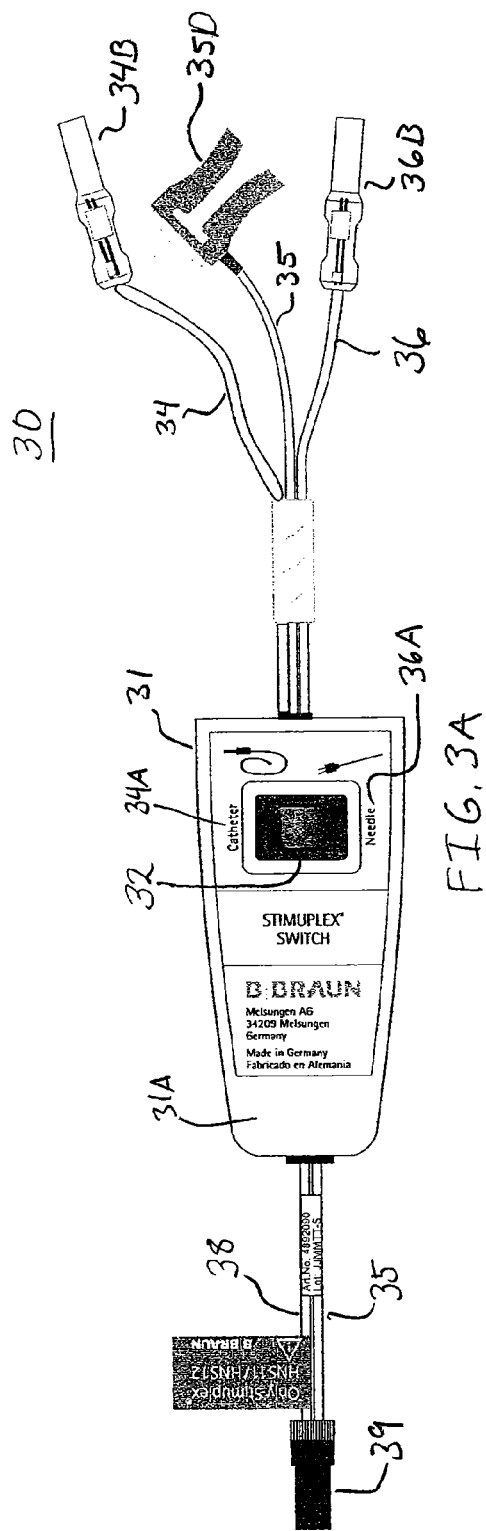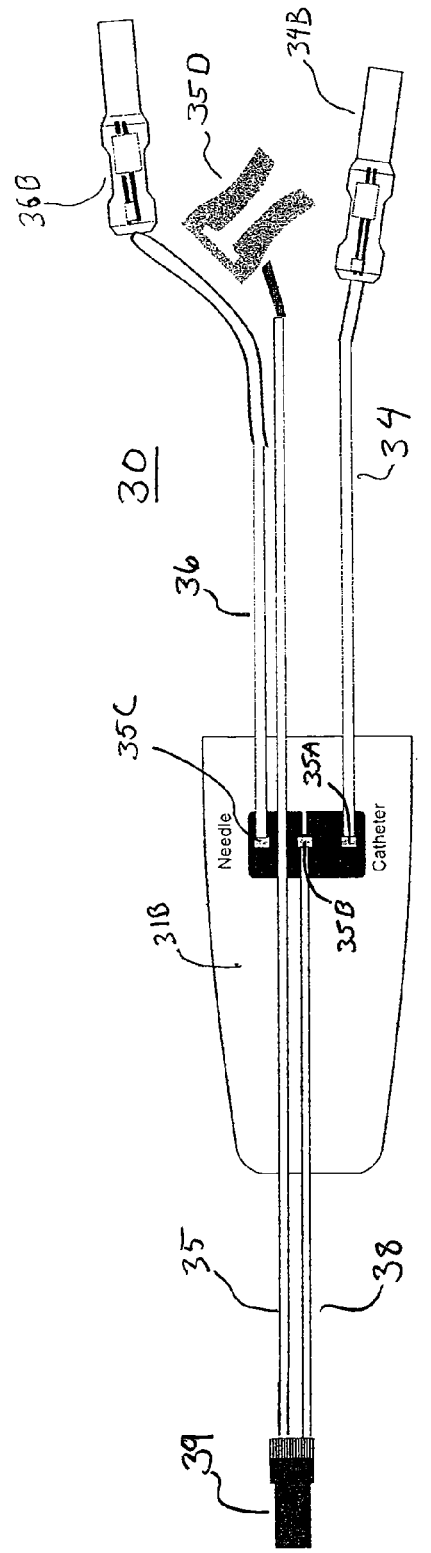

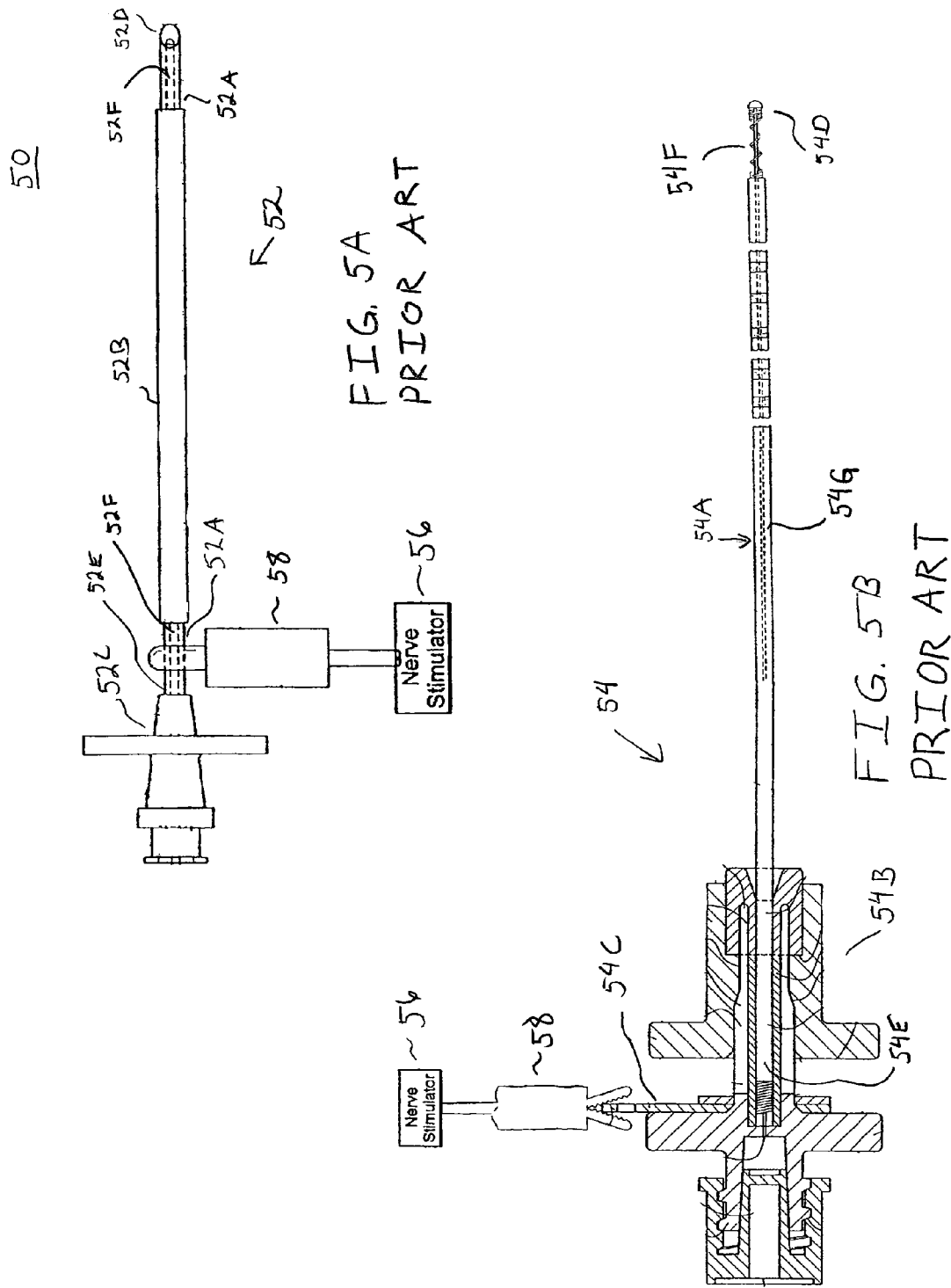

CATHETER SWITCH AND METHOD OF USING A CATHETER SWITCH IN ADMINISTERING A NERVE OR PLEXUS BLOCK

BACKGROUND OF THE INVENTION

A nerve or plexus block is achieved through the administration of variable quantities of an anesthetic agent to a nerve or nerve plexus. Because nerves and nerve plexuses are very fragile structures, not capable of simple repair or reconstruction, it is important to do as little damage as possible in locating the point at which the nerve or plexus may be contacted. Peripheral electrical nerve stimulation is one method that has been proposed for locating medical needles and catheters proximate to nerves and nerve plexuses.

An embodiment of a prior-art peripheral electrical nerve stimulation system 50 for locating and placing needles and catheters proximate to a nerve or plexus is illustrated in FIGS. 5A and 5B. A system similar to system 50 is illustrated and described in U.S. Pat. No. 6,973,346 to Fred Hafer et al., the contents of which are incorporated herein by reference.

System 50 includes a needle assembly 52, a catheter assembly 54, and a nerve stimulator 56. Needle assembly 52 comprises a metal, electrically conductive needle 52A, an insulating coating 52B, and a hub 52C. Needle 52A comprises a proximal end 52E, a distal end 52D, and a hollow, cylindrical cavity 52F that extends the length of needle 52A.

Catheter assembly 54 comprises a catheter 54A, a catheter adapter 54B, and an electrical contact 54C. Catheter 54A is sized so as to be able to be disposed within needle 52A, specifically within cavity 52F of needle 52A, through hub 52C. Catheter 54A comprises a catheter sheath 54G having a proximal end 54E and a distal end 54D. Spanning an interior cavity of catheter sheath 54G extending the entire length of catheter 54A from proximal end 54E to distal end 54D is a coiled wire 54F. Coiled wire 54F is in electrical communication with electrical contact 54C. Catheter sheath 54G is nonconductive and insulates coiled wire 54F along the length of catheter 54A except at distal end 54D where a portion of coiled wire 54F is exposed.

Nerve stimulator 56 attaches to needle assembly 52 through an alligator clamp 58. More specifically, alligator clamp 58 clamps directly to needle 52A to provide an electrical connection from nerve simulator 56 to needle 52A. Nerve stimulator 56 also attaches to catheter assembly 54 through alligator clamp 58. More specifically, alligator clamp 58 clamps to electrical contact 54C to provide an electrical connection from nerve stimulator 56 to coiled wire 54F.

During the administration of a plexus block using system 50, nerve stimulator 56 is clamped to needle assembly 52 using alligator clamp 58. Needle 52A is inserted into a patient and an electrical current provided by nerve stimulator 56 is applied to needle 52A. Insulating coating 52B on needle 52A causes the electrical current conducted by needle 52A to pass through to the portion of needle 52A exposed at distal end 52D. A contraction of a particular observed muscle indicates the proximity of distal end 52D of needle 52A to a plexus of interest in the patient. After the desired plexus is located, alligator clamp 58 is removed from needle 52A and attached to electrical contact 54C of catheter assembly 54.

Catheter 54A is then fed through hub 52C of needle assembly 52, through interior cavity 52F of needle 52A, and out past distal end 52D of needle 52A to a desired position. As with needle 52A, because catheter sheath 54G is nonconductive, current passes through catheter 54A to the patient through the portion of coiled wire 54F exposed at distal end 54D. Again, a contraction of the particular observed muscle indicates the proximity of distal end 54D of catheter 54A to the plexus of interest in the patient. Needle 52A may then be removed, and catheter 54A may be securely fixed. Alligator clamp 58 is then disconnected and anesthetic agents are administered through catheter 54A to the nerve plexus.

SUMMARY OF THE INVENTION

One aspect of the present invention comprises a catheter switch. The catheter switch comprises a first electrical connector for connection to a first medical device, a second electrical connector for connection to a second medical device, and a third electrical connector for connection to a signal source. The catheter switch further comprises an electrical switch coupled to the first, second, and third electrical devices. The electrical switch is configured to include at least two selectable positions, a first position in which the first electrical connector is electrically coupled to the third electrical connector and a second position in which the second electrical connector is electrically coupled to the third electrical connector.

In an exemplary embodiment of the catheter switch, the first medical device is a needle assembly comprising a needle, the second medical device is a catheter assembly comprising a catheter, and the signal source is a nerve stimulator. The first position of the electrical switch is, therefore, for electrically coupling the nerve stimulator to the needle assembly, and the second position of the electrical switch is for electrically coupling the nerve stimulator to the catheter assembly. In a further exemplary embodiment, the electrical switch is a single-pole-double-throw electrical switch.

Another aspect of the present invention comprises a catheter switch assembly. The catheter switch assembly comprises a ground conductor and a catheter switch. The catheter switch comprises a first electrical conductor for electrical communication with a first medical device, a second electrical conductor for electrical communication with a second medical device, a third electrical conductor for electrical communication with a signal source, and an electrical switch coupled to the first, second, and third electrical conductors. The electrical switch is configured to include at least two selectable positions, a first position in which the first electrical conductor is electrically coupled to the third electrical conductor and a second position in which the second electrical conductor is electrically coupled to the third electrical conductor.

In an exemplary embodiment of the catheter switch assembly, the catheter switch assembly further comprises first and second adapter plugs, and the first medical device is a needle assembly comprising a needle, the second medical device is a catheter assembly comprising a catheter, and the signal source is a nerve stimulator. In such an embodiment, the first conductor is terminated in the first adapter plug, and the second conductor is terminated in the second adapter plug. The first adapter plug is for connection to the needle assembly, and the second adapter plug is for connection to the catheter assembly. In a further exemplary embodiment of the catheter switch assembly, the ground connector is terminated in a skin electrode clamp configured to be connectable to a skin electrode.

A further aspect of the present invention comprises a method of using the catheter switch assembly (described above) with a nerve stimulator, a first medical device, and a second medical device in the administration of a nerve or plexus block. The method comprises the steps of applying the ground conductor of the catheter switch assembly to a patient.

The nerve stimulator is operated to provide an electrical current, and the electrical switch of the catheter switch assembly is positioned to select the first position to provide the electrical current of the nerve stimulator to the first medical device. The first medical device is inserted into the patient. Stimulation of a nerve of the patient by the electrical current provided by the nerve stimulator is then observed. The electrical switch is then positioned to select the second position to provide the electrical current of the nerve stimulator to the second medical device. The second medical device is inserted into the patient. Stimulation of the nerve of the patient by the electrical current provided by the nerve stimulator is observed, and a nerve or plexus block is administered via the second medical device.

In an exemplary embodiment of the method, the first medical device comprises a needle assembly comprising a needle comprising a proximal end, a distal end, and a hollow central cavity extending through the needle from the proximal end to the distal end, and the second medical device comprises a catheter assembly comprising a catheter adapted for insertion into the hollow central cavity of the needle. The step of inserting the second medical device into the patient comprises inserting the catheter into the hollow central cavity of the needle, and the step of administering the nerve or plexus block is performed after the step of observing the stimulation of the nerve by the second medical device indicates that a portion of the second medical device is proximate to the nerve of the patient.

BRIEF DESCRIPTION OF THE DRAWINGS

The invention is best understood from the following detailed description when read in connection with the accompanying drawings. Included in the drawings are the following figures:

FIG. 3A is as illustration of a front planar view of a catheter switch assembly comprising a catheter switch and a ground conductor, in accordance with a further exemplary embodiment of the present invention;

FIG. 3B is an illustration of a rear planar view of the catheter switch assembly of FIG. 3A;

FIGS. 5A and 5B illustrate a prior-art system for administering a nerve or plexus block.

DETAILED DESCRIPTION OF THE INVENTION

Figure 1A:
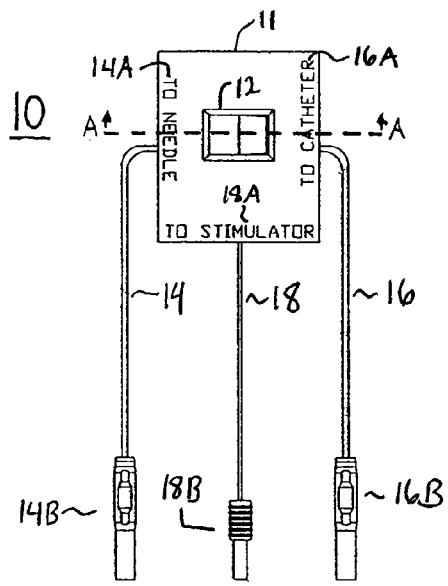
FIG. 1A is an illustration of a front planar view of a catheter switch, in accordance with an exemplary embodiment of the present invention.

Referring now to FIG. 1A, there is illustrated a front planar view of a catheter switch 10 in accordance with an exemplary embodiment of the present invention. Catheter switch 10 comprises an electrical switch 12, at least a portion of which is disposed with housing 11. Catheter switch 10, and more specifically electrical switch 12, comprises two selectable positions, a first position in which a signal source is connected to a first medical device and a second position in which the signal source is connected to a second medical device. As described in more detail below, electrical switch 12 is a single-pole-double-throw ("SPDT") rocker switch.

Catheter switch 10 comprises a first conductor 14 that is terminated in an adapter plug 14B, a second conductor 16 that is terminated in an adapter plug 16B, and a third conductor 18 that is terminated in an adapter plug 18B. Adapter plug 14B is for electrically connecting catheter switch 10 to a first medical device; adapter plug 16B is for electrically connecting catheter switch 10 to a second medical device; and adapter plug 18B is for electrically connecting catheter switch 10 to a signal source.

In the exemplary embodiment illustrated in FIG. 1A, the signal source is a nerve stimulator (identified by label 18A but not illustrated), the first medical device is a needle assembly (identified by label 14A but not illustrated), and the second medical device is a catheter assembly (identified by label 16A but not illustrated). Thus, in the first selectable position of electrical switch 12, a nerve stimulator connected to conductor 18 by adapter plug 18B is electrically coupled to a needle assembly connected to conductor 14 by adapter plug 14B, and in the second selectable position of electrical switch 12, the nerve stimulator is electrically coupled to a catheter assembly connected to conductor 16 by adapter plug 16B. In an exemplary embodiment, adapter plugs 14B and 16B are male-type adapter plugs, and adapter plug 18B is a female-type adapter plug. In another exemplary embodiment, adapter plugs 14B and 16B are female-type adapter plugs, and adapter plug 18B is a male-type adapter plug.

In the exemplary embodiment in which the first medical device is a needle assembly, the second medical device is a catheter assembly, and the signal source is a nerve stimulator, housing 11 may include labels that identify with which adapter plugs the needle assembly, the catheter assembly, and the nerve stimulator are associated. Illustrated in FIG. 1A is a label 14A "TO NEEDLE" that identifies that adapter plug 14B is for connection to a needle assembly comprising a needle. A label 16A "TO CATHETER" identifies that adapter plug 16B is for connection to a catheter assembly comprising a catheter. A label 18A "TO STIMULATOR" identifies that adapter plug 18B is for connection to a nerve stimulator. Additionally, label 14A ("TO NEEDLE") identifies that the first position of electrical switch 12 couples the nerve stimulator (not illustrated) to the needle assembly (not illustrated), and label 16A ("TO CATHETER") identifies that the second position of electrical switch 12 couples the nerve stimulator (not illustrated) to the catheter assembly (not illustrated).

Figure 1B:
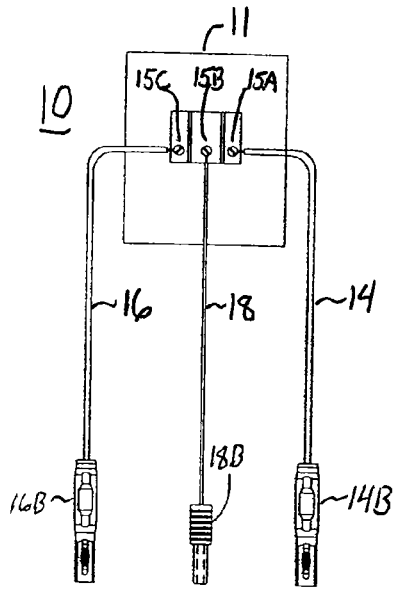
FIG. 1B is an illustration of a rear planar view of the catheter switch of FIG. 1A.

Referring now to FIG. 1B, there is illustrated a rear planar view of catheter switch 10. Attached to the rear portion of housing 11 are electrical connectors 15A, 15B, and 15C. In an exemplary embodiment, electrical connectors 15A, 15B, and 15C are screws, although they are not so limited. In alternative embodiments, electrical connectors 15A, 15B, and 15C may be solder connects, plugs, sockets, etc. Catheter switch 10 is illustrated in FIG. 1B with its rear cover (not illustrated) removed to expose electrical connectors 15A, 15B, and 15C to view. During use of catheter switch 10, the rear cover is in place to protect electrical connectors 15A, 15B, and 15C from accidental grounding, shorting, etc.

Electrical switch 12 is coupled to electrical connectors 15A, 15B, and 15C. Conductor 14 is coupled to electrical connector 15A to couple the first medical device to catheter switch 10 and, more specifically, to electrical switch 12; conductor 16 is coupled to electrical connector 15C to couple the second medical device to catheter switch 10 and, more specifically, to electrical switch 12; and conductor 18 is coupled to electrical connector 15B to couple the signal source to catheter switch 10 and, more specifically, to electrical switch 12.

Referring now to both FIGS. 1A and 1B, label 14A ("TO NEEDLE") also indicates that the first position of electrical switch 12 electrically couples electrical connector 15A to electrical connector 15B, thereby electrically coupling the needle assembly (not illustrated) connected to adapter plug 14B to the nerve stimulator (not illustrated) connected to adapter plug 18B, and label 16A ("TO CATHETER") indicates that the second position of electrical switch 12 electrically couples the electrical connector 15C to electrical connector 15B, thereby electrically coupling the catheter assembly (not illustrated) connected to adapter plug 16B to the nerve stimulator (not illustrated) connected to adapter plug 18B.

Figure 1C:
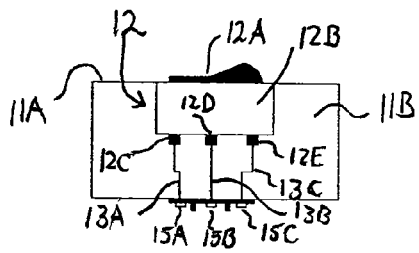
FIG. 1C is an illustration of a cross section of the catheter switch of FIG. 1A along the line A-A illustrated in FIG. 1A.

FIG. 1C illustrates a view of a cross section of catheter switch 10 taken at line A-A illustrated in FIG. 1A. As can be seen in FIG. 1C, electrical switch 12 includes a rocker 12A by which a user may select between the first and second positions of electrical switch 12. Electrical switch 12 also includes a body 12B that contains the terminals 12C, 12D, and 12E of electrical switch 12. As can been seen in FIG. 1C, body 12B of electrical switch 12 is disposed within an interior space 11B of catheter switch 10, but rocker 12A is partially disposed outside housing 11 of catheter switch 10 above top surface 11A. Thus, electrical switch 12 is partially disposed within housing 11.

Electrical switch 12 includes terminals 12C, 12D, and 12E that are coupled to the external connectors 15A, 15B, and 15C of catheter switch 10. Terminal 12C is connected to electrical connector 15A via conductor 13A; terminal 12D is connected to electrical connector 15B via conductor 13B; and terminal 12E is connected to electrical connector 15C via conductor 13C. The illustrated embodiment is a simple schematic figure illustrating the electrical coupling between terminals 12C, 12D, and 12E and respective electrical connectors 15A, 15B, and 15C. Other circuitry, such as filters, anti-bounce circuitry, etc., may be included in serial with, or in place of, one or more of conductors 13A, 13B, and 13C.

Figure 1D:
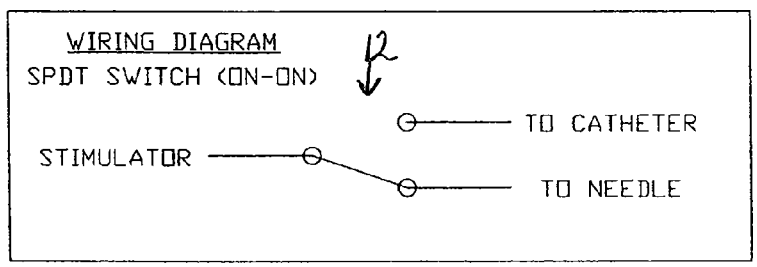
FIG. 1D is an illustration of a wiring diagram of the catheter switch of FIG. 1A.

The wiring diagram illustrated in FIG. 1D provides an illustration of the electrical connections to electrical switch 12. The input terminal of switch 12 is for connection to a nerve stimulator. One of the output terminals of switch 12 is for connection to a catheter assembly, and the other of the output terminals is for connection to a needle assembly. FIG. 1D illustrates that electrical switch 12 is a SPDT switch. The figure also illustrates that electrical switch 12 is in the first position as the input terminal corresponding to the nerve stimulator is connected to the output terminal corresponding to the needle assembly.

Figure 2A:
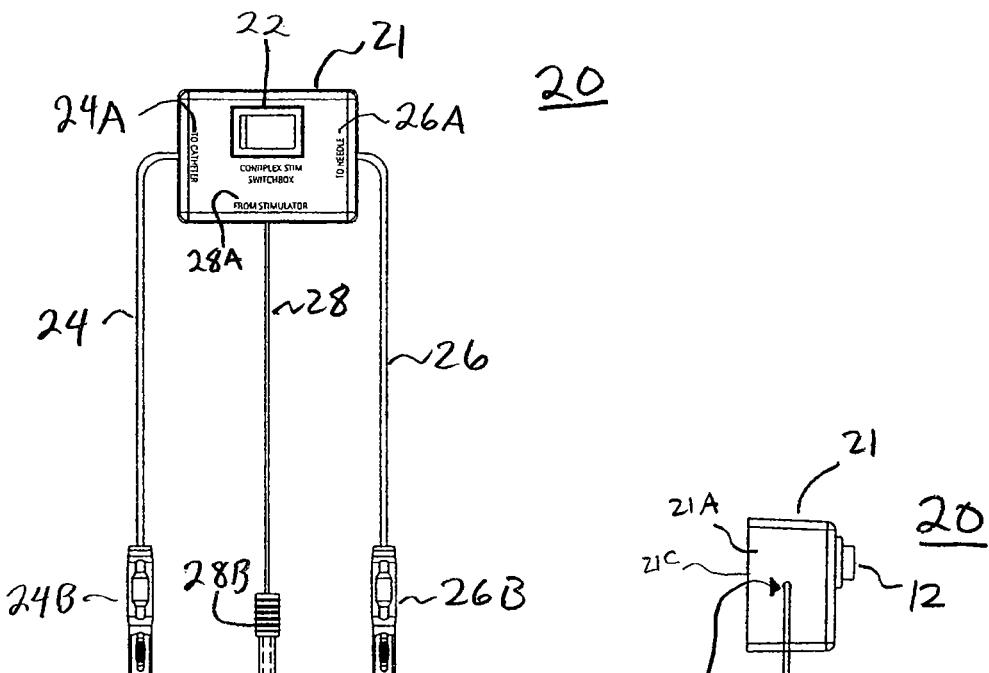
FIG. 2A is an illustration of a front planar view of a catheter switch, in accordance with another exemplary embodiment of the present invention.

Referring now to FIG. 2A, there is illustrated another exemplary embodiment of a catheter switch in accordance with the present invention. In particular, FIG. 2A illustrates a front planar view of a catheter switch 20 comprising a housing 21, an electrical switch 22, labels 24A, 26A, and 28A, electrical conductors 24, 26, and 28, and adapter plugs 24B, 26B, and 28B. Electrical switch 22, labels 24A, 26A, and 28A, electrical conductors 24, 26, and 28, and adapter plugs 24B, 26B, and 28B are respectively similar to electrical switch 12, labels 14A, 16A, and 18A, electrical conductors 14, 16, and 18, and adapter plugs 14B, 16B, and 18B of catheter switch 10. Housing 21, however, differs from housing 11, as is described in more detail below with respect to FIGS. 2B and 2C.

Figure 2C:
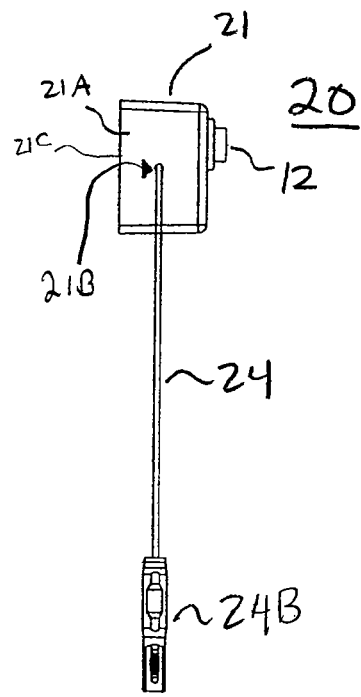
FIG. 2C is an illustration of a side planar view of the catheter switch of FIG. 2A.
Figure 2B:
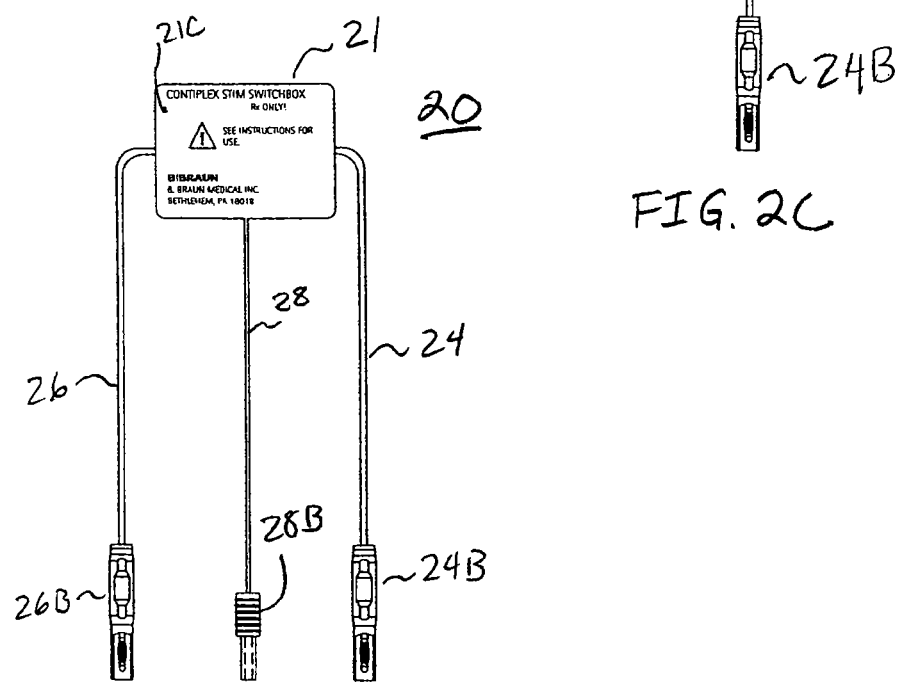
FIG. 2B is an illustration of a rear planar view of the catheter switch of FIG. 2A.

FIG. 2B illustrates a rear planar view of catheter switch 20. As can be seen, rear surface 21C of catheter switch 20 does not include an exposed series of electrical connectors analogous to electrical connectors 15A, 15B, and 15C of catheter switch 10. Instead, the electrical connections (not illustrated) of conductors 24, 26, and 28 to electrical switch 22 are made inside housing 21.

FIG. 2C illustrates a side planar view of catheter switch 20. Included in a side 21A of housing 21, is an opening 21B through which electrical conductor 24 passes. Housing 21 also includes openings (not illustrated) on other sides of housing 21 through which electrical conductors 26 and 28 pass. Because electrical conductors 24, 26, and 28 pass through the sides of housing 21, rear surface 21C of catheter switch 20 is flat. Therefore, catheter switch 20 is able to lie flat on a surgical bench, for example, thereby providing stability to housing 21 while electrical switch 22 is manipulated.

Illustrated in FIG. 3A is a front planar view of a catheter switch assembly 30, and particularly a view of a front surface 31A of a catheter switch assembly 30, in accordance with an exemplary embodiment of the present invention. Catheter switch assembly 30 includes a housing 31, an electrical switch 32, conductors 34, 36, and 38, labels 34A and 36A, and adapter plugs 34B and 36B that are respectively analogous (though not necessarily identical) to housing 11, electrical switch 12, conductors 14, 16, and 18, labels 14A and 16A, and adapter plugs 14B and 16B of catheter switch 10. Catheter switch assembly 30 additionally includes a ground conductor 35 and an adapter plug 39. Conductor 38 and an end of ground conductor 35 are terminated in adapter plug 39. Thus, adapter plug 39 includes two conductors, one coupled to conductor 38 and one coupled to the end of ground conductor 35. The other end of ground conductor 35 is terminated in an skin electrode clamp 35D that is configured to be connectable to a skin electrode placed on a patient. In an exemplary embodiment, skin electrode clamp 35D is an electrocardiogram electrode clamp.

In an exemplary embodiment, adapter plugs 34B and 36B are male-type adapter plugs, and adapter plug 39 is a female-type adapter plug. In another exemplary embodiment, adapter plugs 34B and 36B are female-type adapter plugs, and adapter plug 39 is a male-type adapter plug.

FIG. 3B illustrates a rear planar view of catheter switch assembly 30, and particularly a view of a rear surface 31B of catheter switch assembly 30. Disposed on rear surface 31B are three terminals: terminal 35A, terminal 35B, and terminal 35C. Electrically coupled to terminal 35A is electrical conductor 34; electrically coupled to terminal 35B is electrical conductor 38; and electrically coupled to terminal 35C is electrical conductor 36. Similar to terminals 15A, 15B, and 15C, electrical terminals 35A, 35B, and 35C are coupled to electrical switch 32 so that electrical switch 32 may select to couple a nerve stimulator (not illustrated) attached to adapter plug 39 to a needle assembly (not illustrated) attached to adapter plug 36B or to a catheter assembly (not illustrated) attached to adapter plug 34B. As can be seen in FIG. 3B, ground conductor 35 remains external to housing 31 and makes no electrical connections to electrical switch 32. Catheter switch assembly 30 is illustrated in FIG. 3B with its rear cover (not illustrated) removed to expose terminals 35A, 35B, and 35C to view. During use of catheter switch assembly 30, the rear cover is in place to protect terminals 35A, 35B, and 35C from accidental grounding, shorting, etc.

Figure 4:
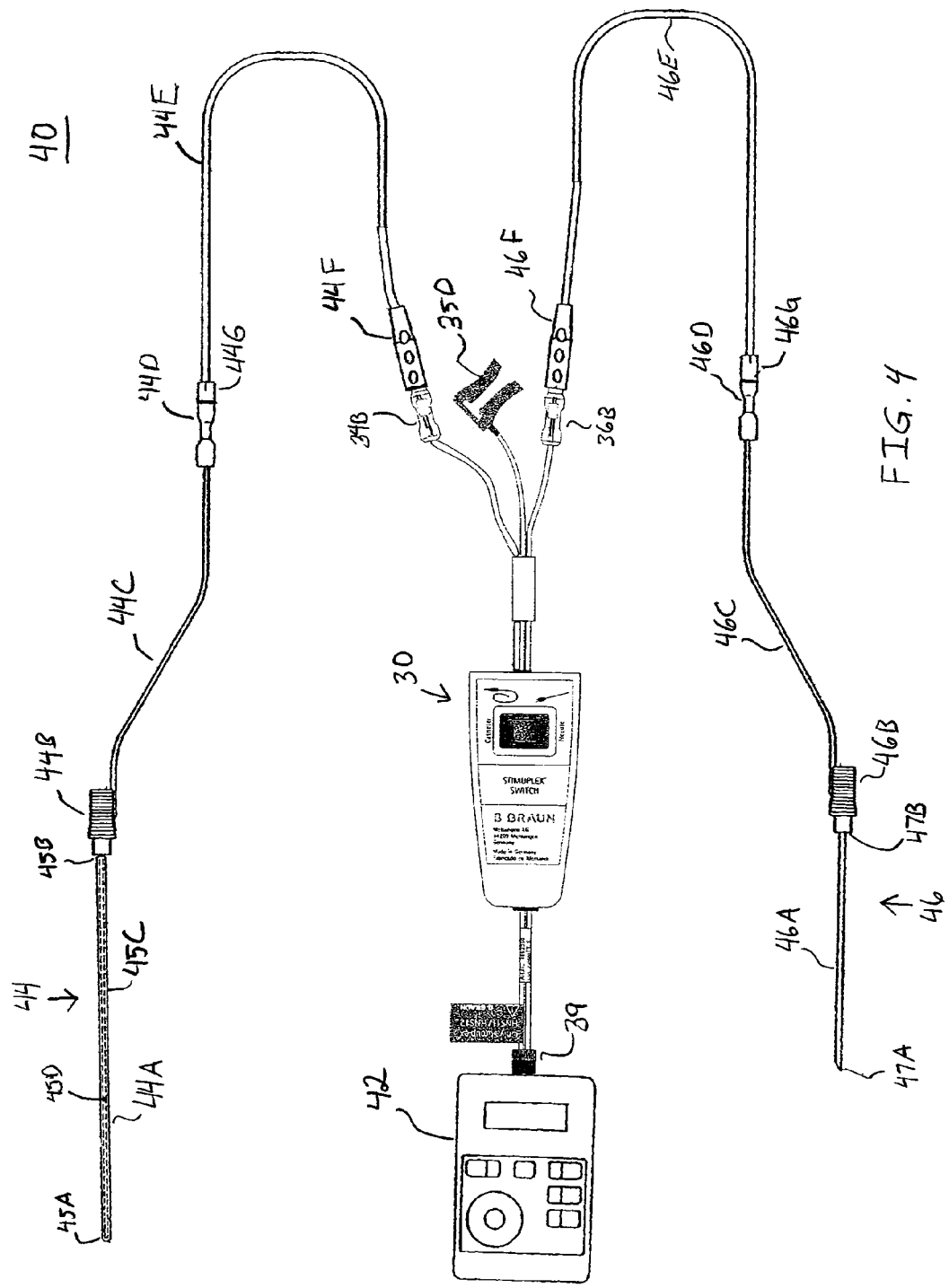
FIG. 4 is an illustration of a catheter switch assembly connected to a nerve stimulator, a needle assembly, and a catheter assembly, in accordance with yet another exemplary embodiment of the present invention.

Referring now to FIG. 4, there is illustrated a catheter switch assembly system 40 comprising the catheter switch assembly 30 of FIG. 3A connected to a nerve stimulator 42, a catheter assembly 44, and a needle assembly 46. Catheter assembly 44 includes a catheter 44A secured to a hub 44B. Connected to hub 44B is an electrical conductor 44C. Thus, hub 44B electrically couples electrical conductor 44C to catheter 44A. Electrical conductor 44C is terminated in an adapter plug 44D.

Catheter 44A comprises a sheath 45C that includes a hollow central cavity 45D that extends from distal end 45A to proximal end 45B. Distal end 45A of catheter 44A is open to expose cavity 45D, and proximal end 45B of catheter 44A is open to hub 44B so that fluid may be injected into hub 44B and administered through cavity 45D and out distal end 45A into a patient. Although not illustrated, catheter 44A includes a conductor disposed within cavity 45D. Sheath 45C is made of a nonconductive material, and a portion of the interior conductor is exposed at distal end 45A. The internal conductor is coupled to electrical conductor 44C by hub 44B.

An electrical conductor 44E connects catheter assembly 44 and associated cabling 44C to catheter switch assembly 30. Conductor 44E allows catheter assembly 44 to be placed at a distance from catheter switch assembly 30. Conductor 44E is terminated at both ends by adapter plugs 44F and 44G. Adapter plug 44G is connected to adapter plug 44D, and adapter plug 44F is connected to adapter plug 34B of catheter switch assembly 30. In another embodiment of catheter switch assembly system 40, adapter plug 44D connects directly to adapter plug 34B.

Needle assembly 46 includes a metal, electrically conductive needle 46A that comprises a proximal end 47B secured to a hub 46B and a distal end 47A comprising a sharp tip. Extending inside needle 46A between proximal end 47B through to distal end 47A is a hollow cylindrical cavity (not illustrated). The cavity is open at distal end 47A and is open to hub 46B at proximal end 47B. It is sized to accommodate catheter 44A inserted through hub 46B and out through distal end 47A. Although not illustrated, needle 46A includes an insulating sheath such that only a portion of the conductive metal of needle 46A proximate to distal end 47A is exposed.

Connected to hub 46B is an electrical conductor 46C. Hub 46B electrically couples electrical conductor 46C to needle 46A while allowing catheter 44A to be inserted within hub 46B and into needle 46A. Electrical conductor 46C is terminated in an adapter plug 46D.

An electrical conductor 46E connects needle assembly 46 and associated cabling 46C to catheter switch assembly 30. Conductor 46E allows needle assembly 46 to be placed at a distance from catheter switch assembly 30. Conductor 46E is terminated at both ends by adapter plugs 46F and 46G. Adapter plug 46G is connected to adapter plug 46D, and adapter plug 46F is connected to adapter plug 36B of catheter switch assembly 30. In another embodiment of catheter switch assembly system 40, adapter plug 46D connects directly to adapter plug 36B.

Adapter plug 39 of catheter switch assembly 30 is connected to nerve stimulator 42. Nerve stimulator 42 provides a series electrical pulses and the ability to adjust the frequency, pulse widths, and pulse amplitudes of the pulses. In an exemplary embodiment, nerve stimulator 42 is capable of providing pulses having a frequency range of 1 Hz to 2 Hz, a pulse-width range of 0.1 ms to 1.0 ms, and a pulse-amplitude of 0 mA to 5.0 mA. A user of nerve stimulator 42 may select precise values within these ranges to command nerve stimulator 42 to provide a pulse train having a particular frequency, pulse width, and pulse amplitude. An exemplary embodiment of nerve stimulator 42 is the Stimuplex® HNS11 peripheral nerve stimulator manufactured by B. Braun Medical Inc.

Nerve stimulator 42 provides the electrical pulses to catheter switch assembly 30. As described above, catheter switch assembly 30 may selectively couple adapter plug 39 to adapter plug 34B or 36B. Thus, catheter switch assembly 30 may select to provide the electrical pulses generated by nerve stimulator 42 to either catheter assembly 44 or to needle assembly 46.

An exemplary method of using catheter switch assembly system 40 in the administration of a nerve or nerve plexus block to a patient is now described. A skin electrode (not shown) is applied to a patient in the vicinity of the nerve to the anesthetized. Electrode clamp 35D is clamped to the skin electrode. The anesthetist positions electrical switch 32 in catheter switch assembly 30 to select the first position (which selects needle assembly 46) and operates nerve stimulator 42 to provide a train of electrical pulses to needle assembly 46. Using nerve stimulator 42, the anesthetist configures the pulse train to have pulse widths of 0.1 ms to 1.0, a pulse frequency of 1 Hz to 2 Hz, and pulse amplitudes of 0 mA to 5 mA. Precise values depend on the nerve to be stimulated and then anesthetized.

The anesthetist then inserts distal end 47A of needle 46A into the patient. While reducing the current (pulse amplitude) outputted by nerve stimulator 42, the anesthetist advances needle 46A into the patient while observing for muscle twitches which indicate that the distal end 47A of needle 46A is proximate to a nerve of interest. When the anesthetist observes a twitch of a muscle corresponding to the desired nerve to be anesthetized and the pulse amplitude of nerve stimulator 42 has reached a lower threshold, the placement of needle end 47A is deemed sufficient and needle 46A is moved no more.

The anesthetist then positions electrical switch 32 in catheter switch assembly 30 to select the second position (which selects catheter assembly 44). Electrical pulses are thereby provided by nerve stimulator 42 to catheter assembly 44. Using nerve stimulator 42, the anesthetist configures the pulse train to have pulse widths of 0.1 ms to 1.0 ms, a pulse frequency of 1 Hz to 2 Hz, and pulse amplitudes of 0 mA to 5 mA. Catheter 44A is inserted into the patient by inserting it into hub 46B of needle assembly 46, through the interior cavity of needle 46A, and out distal end 47A of needle 46A. While reducing the current (pulse amplitude) outputted by nerve stimulator 42, the anesthetist advances catheter 44A into the patient while observing for twitches in the muscle corresponding to the nerve of interest. When the anesthetist observes the muscle twitching and the pulse amplitude of nerve stimulator 42 has reached a lower threshold, the placement of catheter end 45A is deemed sufficient and catheter 44A is moved no more. The nurse then administers a nerve or nerve plexus block through catheter 44A.

Although the invention is illustrated and described herein with reference to specific embodiments, the invention is not intended to be limited to the details shown. Rather, various modifications may be made in the details within the scope and range of equivalents of the claims and without departing from the invention.

What is claimed:
1. A catheter switch comprising:
   a first electrical connector releaseably coupled to a first medical device for repeated attachment to and detachment from the first medical device in a location external to a patient;

a second electrical connector releaseably coupled to a second medical device for repeated attachment to and detachment from the second medical device at a location external to a patient;
a third electrical connector releaseably coupled to a signal source for repeated attachment to and detachment from the signal source at a location external to a patient; and
an electrical switch coupled to the first, second, and third electrical connectors,
wherein the electrical switch is configured to include at least two selectable positions, a first position in which the first electrical connector is electrically coupled to the third electrical connector and a second position in which the second electrical connector is electrically coupled to the third electrical connector.

2. The catheter switch of claim 1, wherein the first medical device is a needle assembly comprising a needle, the second medical device is a catheter assembly comprising a catheter, and the signal source is a nerve stimulator.

3. The catheter switch of claim 1, wherein the electrical switch is a single-pole-double-throw switch.

4. The catheter switch of claim 1, wherein the electrical switch is a single-pole-double-throw rocker switch.

5. The catheter switch of claim 1, further comprising:
a first conductor coupled to the first electrical connector;
a second conductor coupled to the second electrical connector; and
a third conductor coupled to the third electrical connector,
wherein the first electrical connector is for connecting to the first medical device via the first conductor, the second electrical connector is for connecting to the second medical device via the second conductor, and the third electrical connector is for connecting to the signal source via the third conductor.

6. The catheter switch of claim 5, wherein the first conductor is terminated in a first adapter plug and the second conductor is terminated in a second adapter plug.

7. The catheter switch of claim 6, wherein the third conductor is terminated in a third adapter plug.

8. The catheter switch of claim 7, wherein the first and second adapter plugs are female adapter plugs and the third adapter plug is a male adapter plug.

9. The catheter switch of claim 7, wherein the first and second adapter plugs are male adapter plugs and the third adapter plug is a female adapter plug.

10. The catheter switch of claim 1, further comprising a housing in which at least a portion of the electrical switch is disposed.

11. The catheter switch of claim 10, further comprising a first label and a second label attached to the housing, the first label indicating that the first position of the electrical switch electrically couples the first electrical connector to the third electrical connector and the second label indicating that the second position of the electrical switch electrically couples the second electrical connector to the third electrical connector.

12. A catheter switch assembly comprising:
a ground conductor; and
a catheter switch comprising:
a first electrical conductor releaseably coupled with a first medical device for repeated attachment to and detachment from the first medical device in a location external to a patient;
a second electrical conductor releaseably coupled with a second medical device for repeated attachment to and detachment from the second medical device at a location external to a patient;
a third electrical conductor releaseably coupled with a signal source for repeated attachment to and detachment from the signal source at a location external to a patient; and
an electrical switch coupled to the first, second, and third electrical conductors,
wherein the electrical switch is configured to include at least two selectable positions, a first position in which the first electrical conductor is electrically coupled to the third electrical conductor and a second position in which the second electrical conductor is electrically coupled to the third electrical conductor.

13. The catheter switch assembly of claim 12, further comprising first and second adapter plugs, wherein the first conductor is terminated in the first adapter plug and the second conductor is terminated in the second adapter plug.

14. The catheter switch assembly of claim 13, further comprising a nerve stimulator coupled to the electrical switch via the third conductor and coupled to the ground conductor, wherein the signal source is the nerve stimulator.

15. The catheter switch assembly of claim 13, further comprising a third adapter plug, wherein the third conductor and a first end of the ground conductor are terminated in the third adapter plug.

16. The catheter switch assembly of claim 15, wherein a second end of the ground connector is terminated in an electrode clamp configured to be connectable to a skin electrode.

17. The catheter switch assembly of claim 15, wherein the first and second adapter plugs are male adapter plugs and the third adapter plug is a female adapter plug.

18. The catheter switch assembly of claim 15, wherein the first and second adapter plugs are female adapter plugs and the third adapter plug is a male adapter plug.

19. The catheter switch assembly of claim 12, wherein the electrical switch is a single-pole-double-throw switch.

20. The catheter switch of claim 12, wherein the electrical switch is a single-pole-double-throw rocker switch.

21. The catheter switch assembly of claim 12, further comprising a housing in which at least a portion of the electrical switch is disposed.

22. The catheter switch assembly of claim 21, further comprising a first label and a second label attached to the housing, the first label indicating that the first position of the electrical switch electrically couples the first electrical conductor to the third electrical conductor and the second label indicating that the second position of the electrical switch electrically couples the second electrical conductor to the third electrical conductor.

* * * * *